(12) United States Patent
Abbasi

(10) Patent No.: US 11,779,352 B1
(45) Date of Patent: Oct. 10, 2023

(54) TRANS-FACET OBLIQUE LATERAL LUMBAR INTERBODY FUSION

(71) Applicant: Advance Research System, LLC, Edina, MN (US)

(72) Inventor: Hamid R. Abbasi, Edina, MN (US)

(73) Assignee: Advance Research System, LLC, Edina, MN (US)

( * ) Notice: Subject to any disclaimer, the term of this patent is extended or adjusted under 35 U.S.C. 154(b) by 41 days.

(21) Appl. No.: 17/676,575

(22) Filed: Feb. 21, 2022

Related U.S. Application Data

(60) Provisional application No. 63/151,999, filed on Feb. 22, 2021.

(51) Int. Cl.
    *A61B 17/16* (2006.01)
    *A61B 17/17* (2006.01)
    *A61F 2/44* (2006.01)

(52) U.S. Cl.
    CPC ...... *A61B 17/1671* (2013.01); *A61B 17/1757* (2013.01); *A61F 2/4455* (2013.01)

(58) Field of Classification Search
    CPC .................. A61B 17/1671; A61B 17/1757
    See application file for complete search history.

(56) References Cited

U.S. PATENT DOCUMENTS

| | | | | |
|---|---|---|---|---|
| 2,808,826 A | * | 10/1957 | Reiner | A61B 5/05 323/911 |
| 2,919,692 A | * | 1/1960 | Ackermann | A61B 17/1671 606/184 |
| 4,059,115 A | * | 11/1977 | Jumashev | A61B 17/1671 408/36 |
| 5,196,015 A | * | 3/1993 | Neubardt | A61B 17/8875 606/279 |
| 2004/0127963 A1 | * | 7/2004 | Uchida | A61B 17/1671 607/113 |
| 2008/0183188 A1 | * | 7/2008 | Carls | A61B 90/36 606/130 |

OTHER PUBLICATIONS

Abbasi, et al., "Oblique Lateral Lumbar Interbody Fusion (OLLIF): Technical Notes and Early Results of a Single Surgeon Comparative Study" *Cureus*, Oct. 2015; 7(10): e351, https://www.nc___bi.nlm.nih.gov/pmc/articles/PMC4652919/#__ffn_sectitle, last visited (Feb. 18, 2021).

* cited by examiner

*Primary Examiner* — Christian A Sevilla
(74) *Attorney, Agent, or Firm* — Christensen, Fonder, Dardi & Herbert PLLC; Stuart J. Olstad

(57) ABSTRACT

A trans-facet procedure for preparing a patient for oblique lateral lumbar interbody fusion (OLLIF). The preparation procedure includes providing a kit with instruments for accessing Kambin's triangle through bone at nominal approaches preferred for the OLLIF procedure, and providing instructions for the procedure on a non-transitory tangible medium.

24 Claims, 20 Drawing Sheets

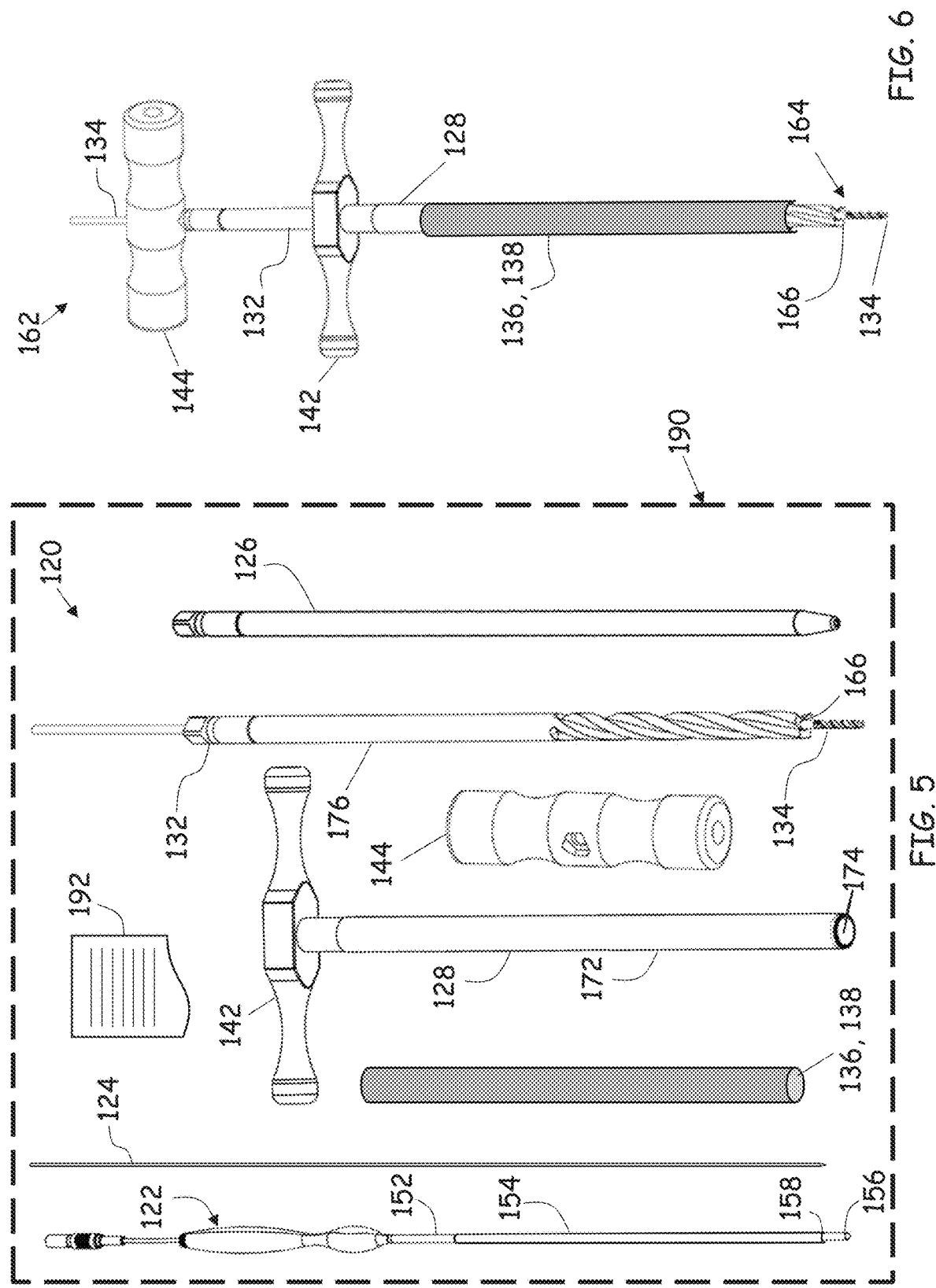

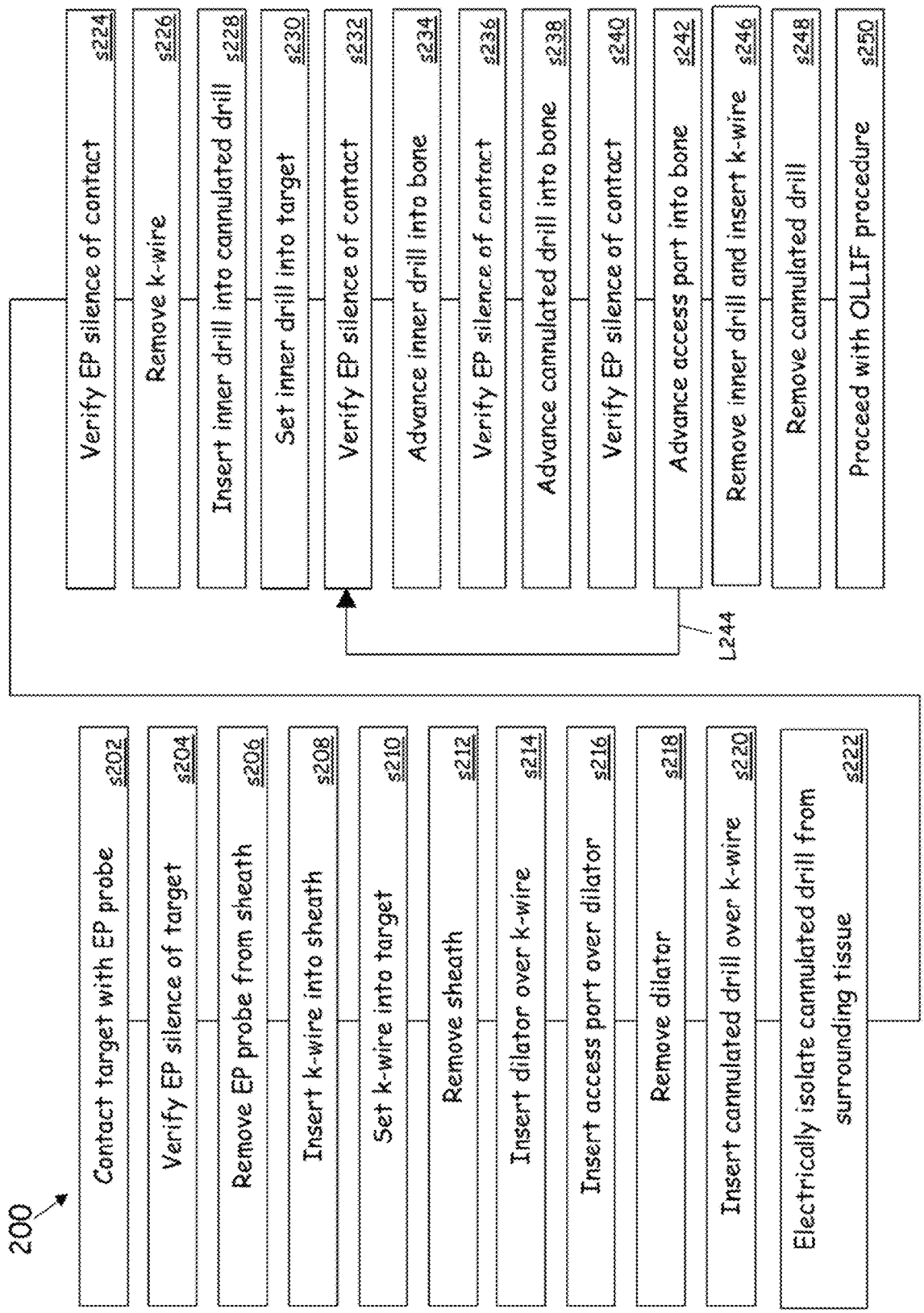

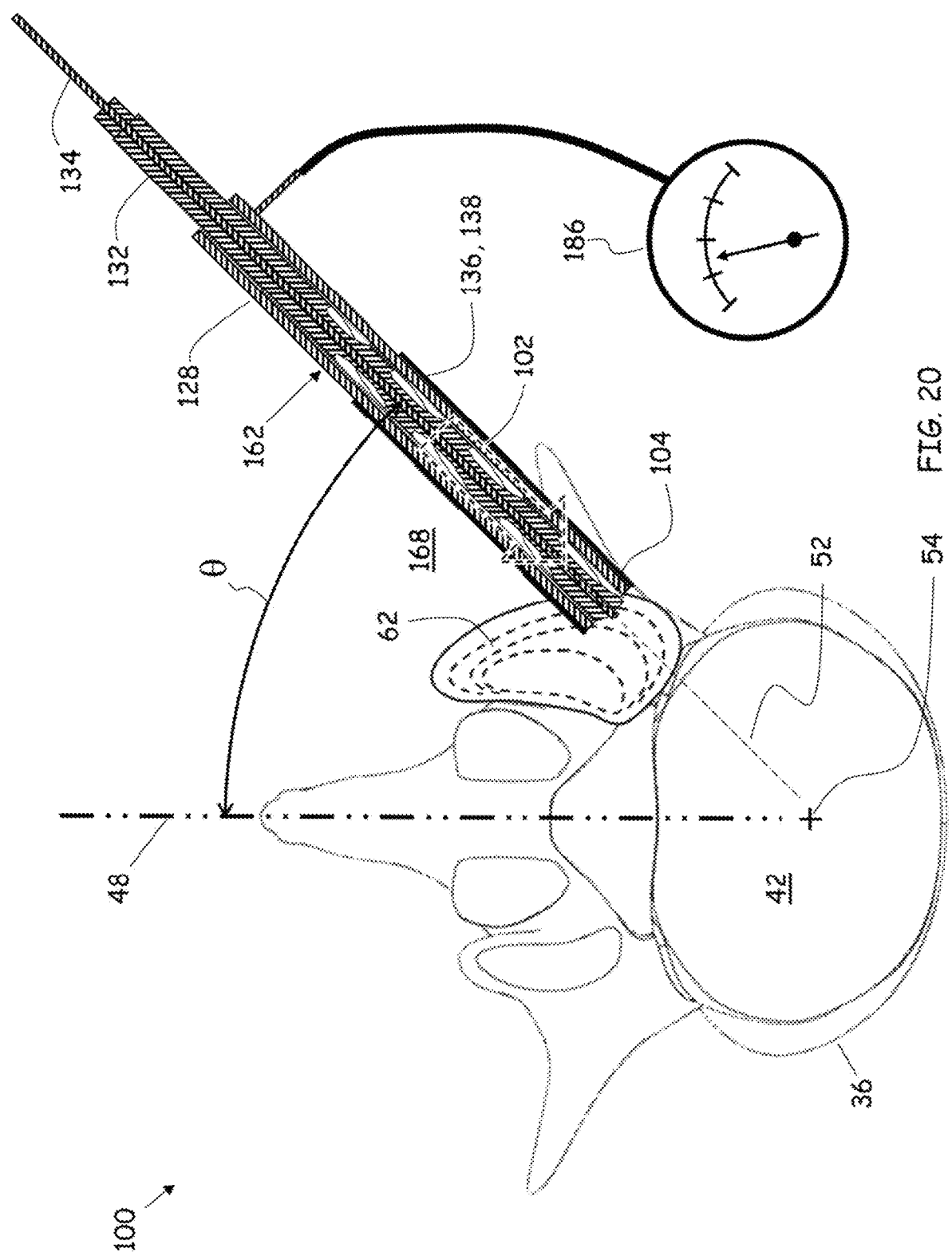

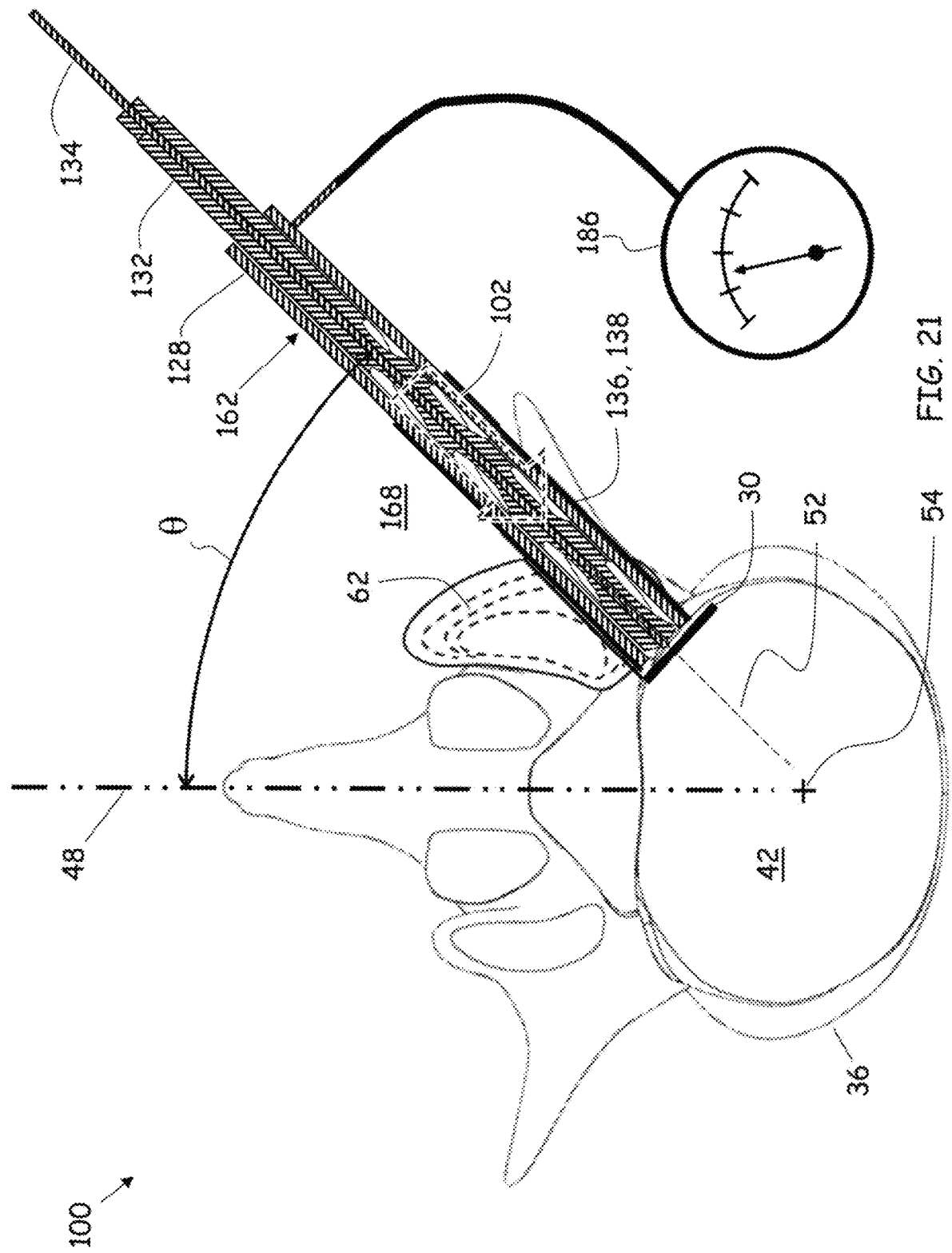

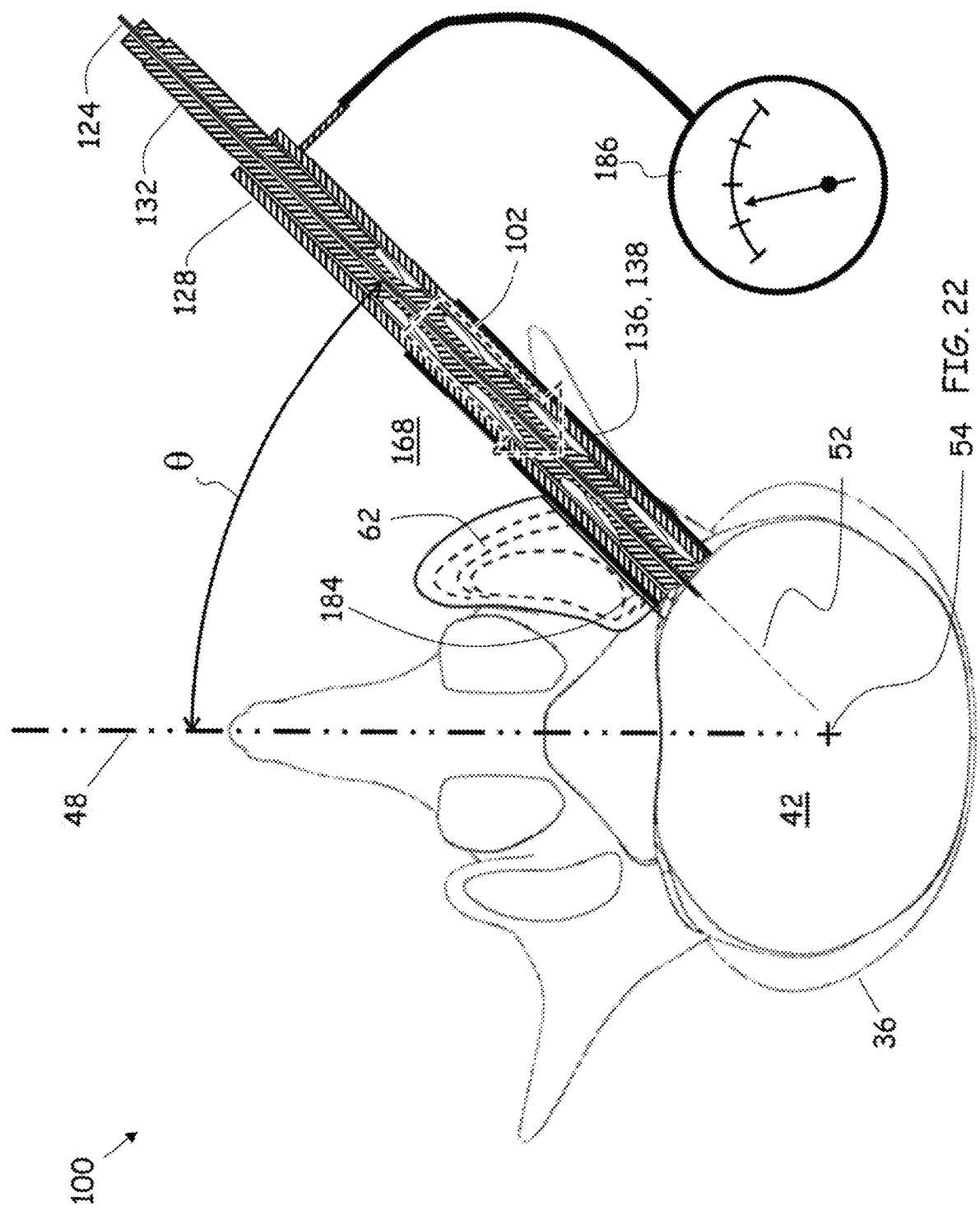

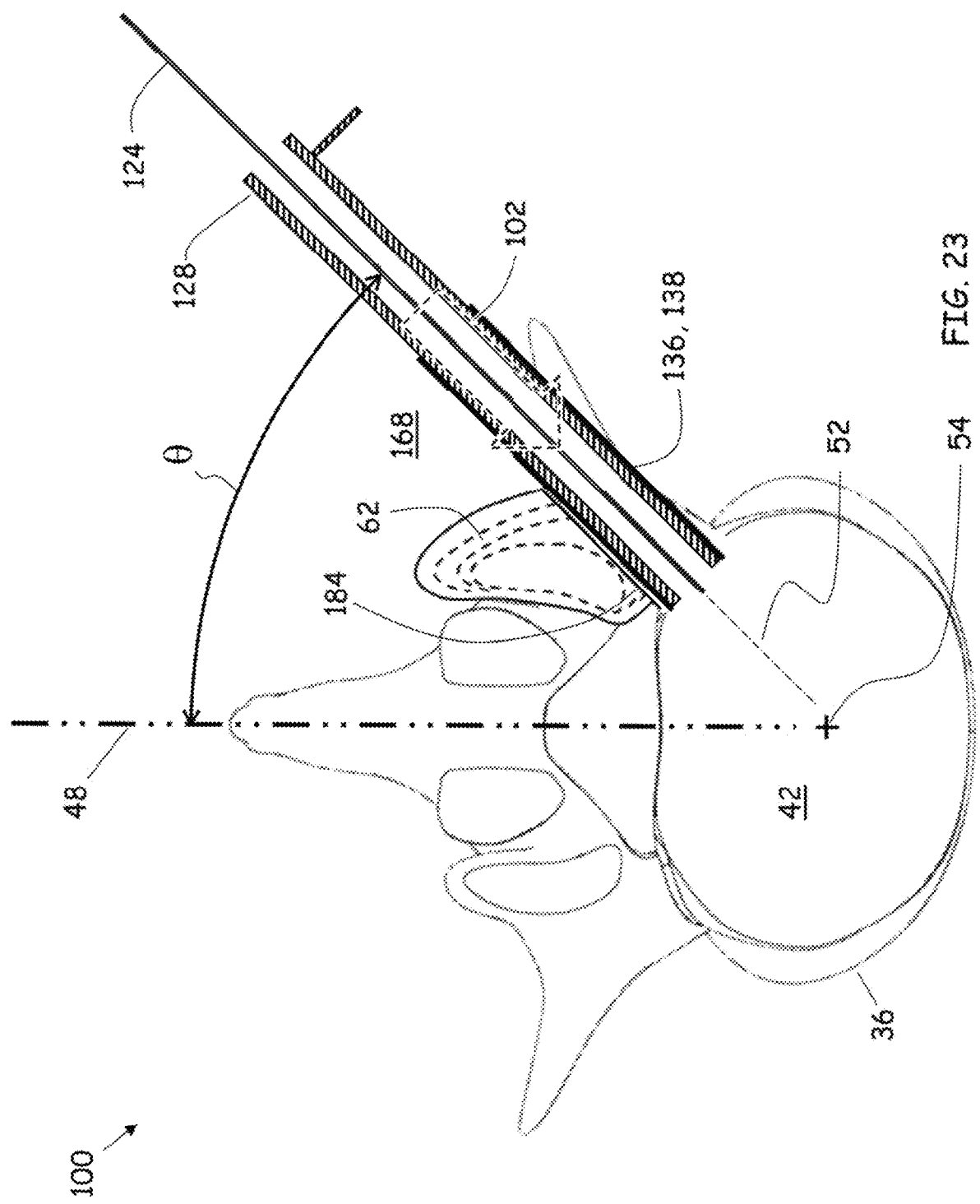

TRANS-FACET OBLIQUE LATERAL LUMBAR INTERBODY FUSION

RELATED APPLICATIONS

This application claims the benefit of U.S. Provisional Application No. 63/151,999, filed Feb. 22, 2021, the disclosure of which is incorporated by reference herein in its entirety.

FIELD OF THE DISCLOSURE

This disclosure is directed generally to products and techniques for interbody fusion of the spinal vertebrae and more specifically to products and techniques for a trans-facet approach to oblique lateral lumbar interbody fusion.

BACKGROUND

Oblique lateral lumbar interbody fusion (OLLIF) is a technique that enables fusion of the lumbar spine through a single incision of 10-15 millimeters, with faster surgery times and an easier approach than other interbody fusion techniques. The OLLIF procedure involves performing interbody fusion surgery via Kambin's triangle 30 (FIG. 1). Kambin's triangle 30 is an electrophysiologically silent area bounded by an exiting nerve root 32, a superior border 34 of an inferior vertebra 36, and a superior articular process 38 of the inferior vertebra 36, through which an intervertebral disc 42 between the inferior vertebra 36 and a superior vertebra 44 can be accessed. The OLLIF procedure may also implement electrophysiological monitoring, thereby eliminating the need for direct visual reference during surgery. The OLLIF procedure is described in greater detail at Abbasi et al., "Oblique Lateral Lumbar Interbody Fusion (OLLIF): Technical Notes and Early Results of a Single Surgeon Comparative Study" *Cureus*, 2015 October; 7(10): e351 (https://www.ncbi.nlm.nih.gov/pmc/articles/PMC4652919/#_ffn_sectitle, last visited Feb. 18, 2021), the content of which is hereby incorporated by reference herein in its entirety except for express definitions contained therein.

For standard OLLIF procedures, a nominal approach 46 to Kambin's triangle 30 is preferably at an approach angle θ that is approximately 45 degrees (FIG. 2). Herein, the approach angle θ is defined as a posterolateral angle measured relative to the sagittal plane 48. At the approach angle θ of 45 degrees, a trajectory 52 of the approach passes proximate a center 54 of the intervertebral disc 42. Preferred access to Kambin's triangle for the OLLIF procedure may be at approach angles other than 45 degrees, as dictated, for example, by the idiosyncrasies of the patient being treated. That is, an approach variance Δθ of the nominal approach 46 may cause the approach angle θ to be somewhat smaller than 45 degrees, or, in some instances, substantially greater than 45 degrees.

The idiosyncrasies of the patient may include bone or bone growth 62 or other tissue proximate a facet joint 64 (FIG. 3). Anatomical structures experiencing such growth include, but are not limited to, the superior articular process 38 of the inferior vertebra 36, as well as an inferior articular process 66 of the superior vertebra 44. Such bone growth 62 is common for older patients or patients who have experienced spine trauma, both being strong demographics for the OLLIF procedure. The bone or bone growth 62 may obscure the pathway to Kambin's triangle 30, forcing an increase in the approach angle θ that is well beyond the nominal 45 degrees preferred for the OLLIF procedure. The increased approach angle θ causes a narrower projection of Kambin's triangle 30 and may alter the trajectory 52 to be far from the center 54 of the intervertebral disc 42. What is needed is a procedure that enables better control of the approach angle θ for the OLLIF procedure in the presence of bone or bone growth 62 or other idiosyncrasies of the patient.

SUMMARY OF THE DISCLOSURE

Various embodiments of the disclosure include "trans-facet" techniques and methods that enable favorable approach angles to Kambin's triangle for OLLIF procedures, even in the presence of excessive tissue growth. The trans-facet method enables a wider range of approach angles than are normally available for the OLLIF procedure, thereby providing greater autonomy for the surgeon. Surgical instruments are also disclosed for rapid and efficient execution of the method.

Standard OLLIF procedures do not involve penetration that passes through bone structures. While some level of manipulation may be implemented during the OLLIF procedure to expand Kambin's triangle, the bone structures adjacent Kambin's triangle are left largely intact, with only incidental removal of bone material. The disclosed trans-facet OLLIF technique involves boring through bone structures that are proximate the facet, providing access to Kambin's triangle at favorable approach angles for conducting the OLLIF procedure through the resultant bore. Furthermore, the trans-facet OLLIF technique presented herein retains the electrophysiological monitoring aspect during the formation of the bore, thereby eliminating the need for direct visual reference.

BRIEF DESCRIPTION OF THE DRAWINGS

FIG. 5 is a perspective view of instruments for a trans-facet OLLIF procedure according to an embodiment of the disclosure;

FIG. 6 is a perspective view of a boring assembly for a trans-facet OLLIF procedure according to an embodiment of the disclosure;

FIG. 7 is a flow diagram of a trans-facet OLLIF procedure according to an embodiment of the disclosure; and FIGS. 8 through 23 are sectional schematic views of certain steps of the trans-facet OLLIF procedure of FIG. 7 according to an embodiment of the disclosure.

DETAILED DESCRIPTION OF THE DRAWINGS

Figure 1:
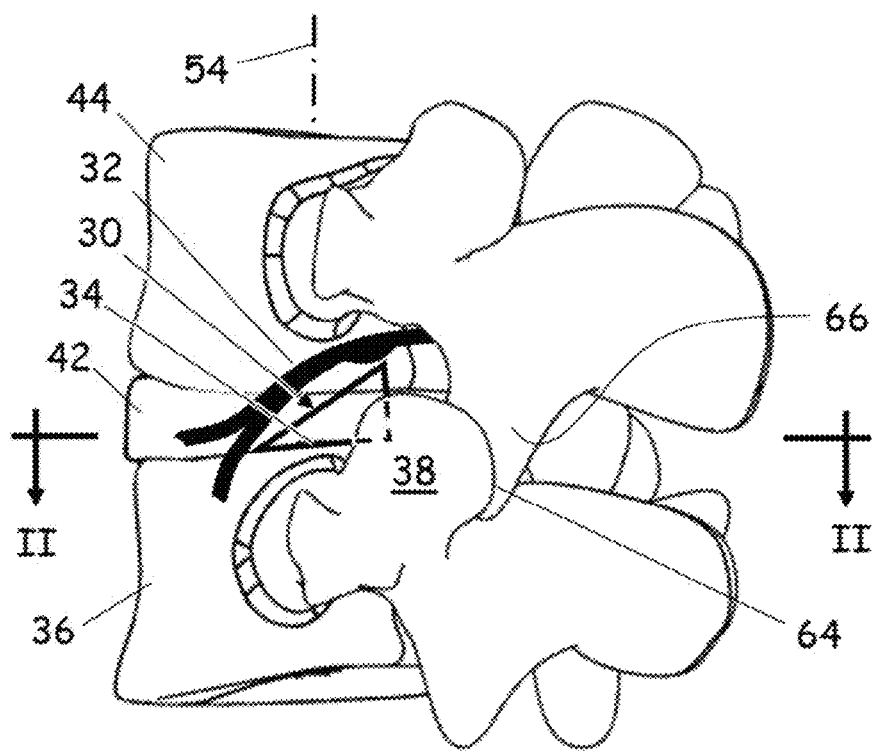
FIG. 1 is a perspective posterolateral view of adjacent lumbar vertebrae and Kambin's triangle as seen from a nominal approach for an oblique lateral lumbar interbody fusion (OLLIF) procedure.
Figure 2:
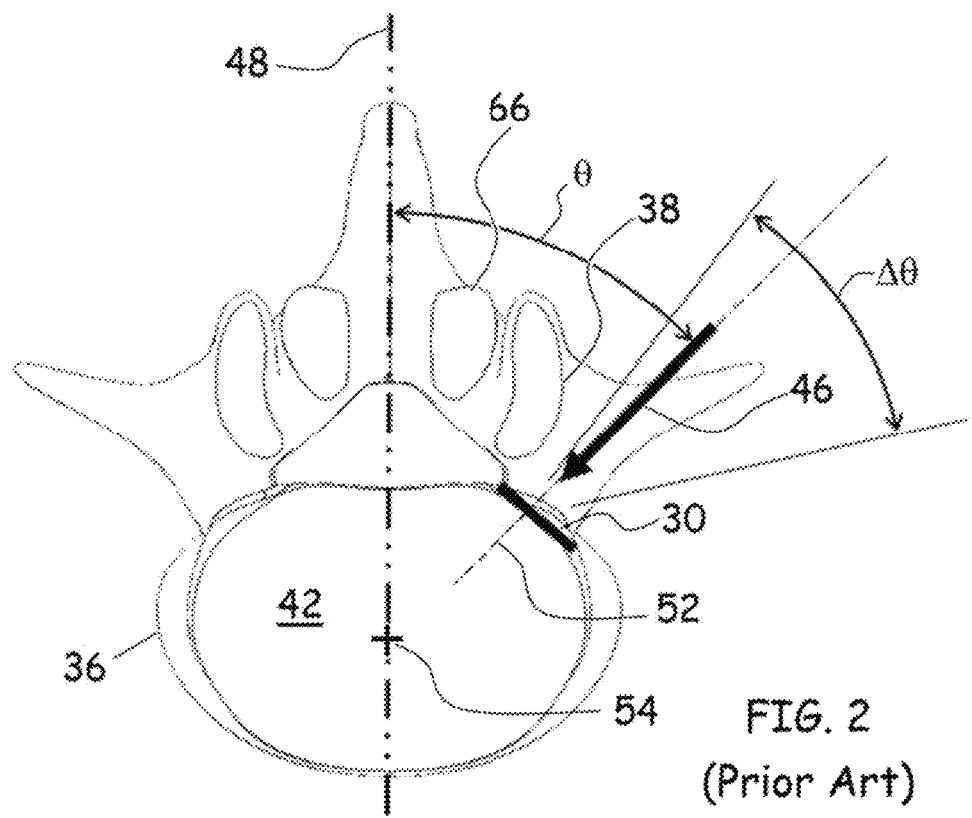
FIG. 2 is a sectional view at plane II-II of FIG. 1, depicting typical approaches for the OLLIF procedure.
Figure 3:
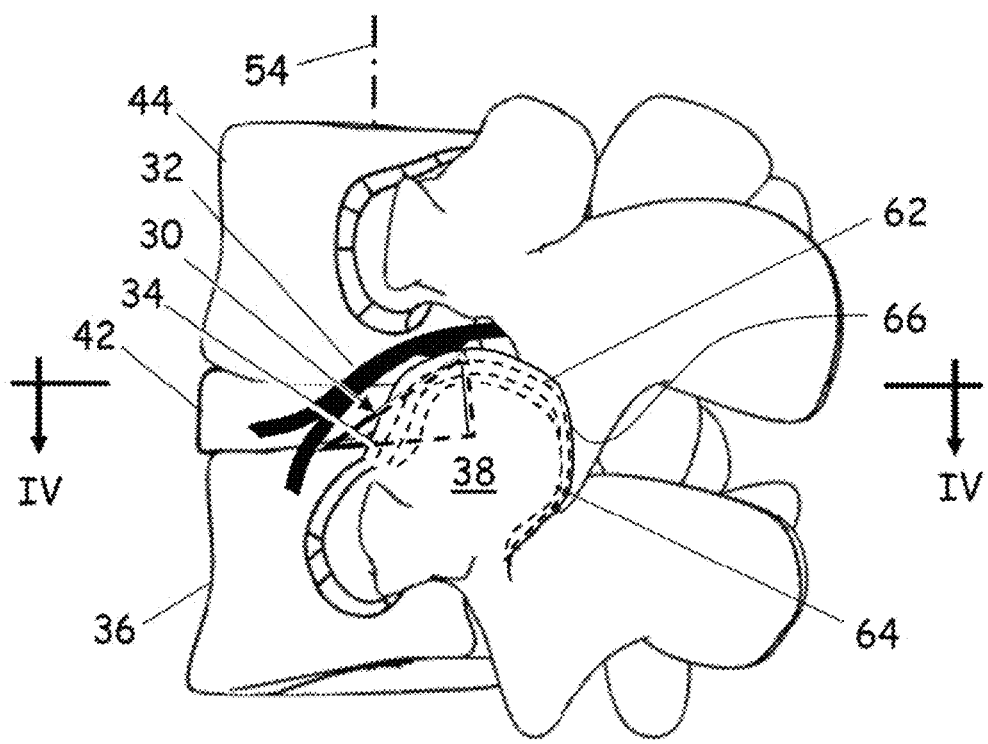
FIG. 3 is the perspective posterolateral view of FIG. 1 with bone growth that obscures Kambin's triangle.
Figure 4:
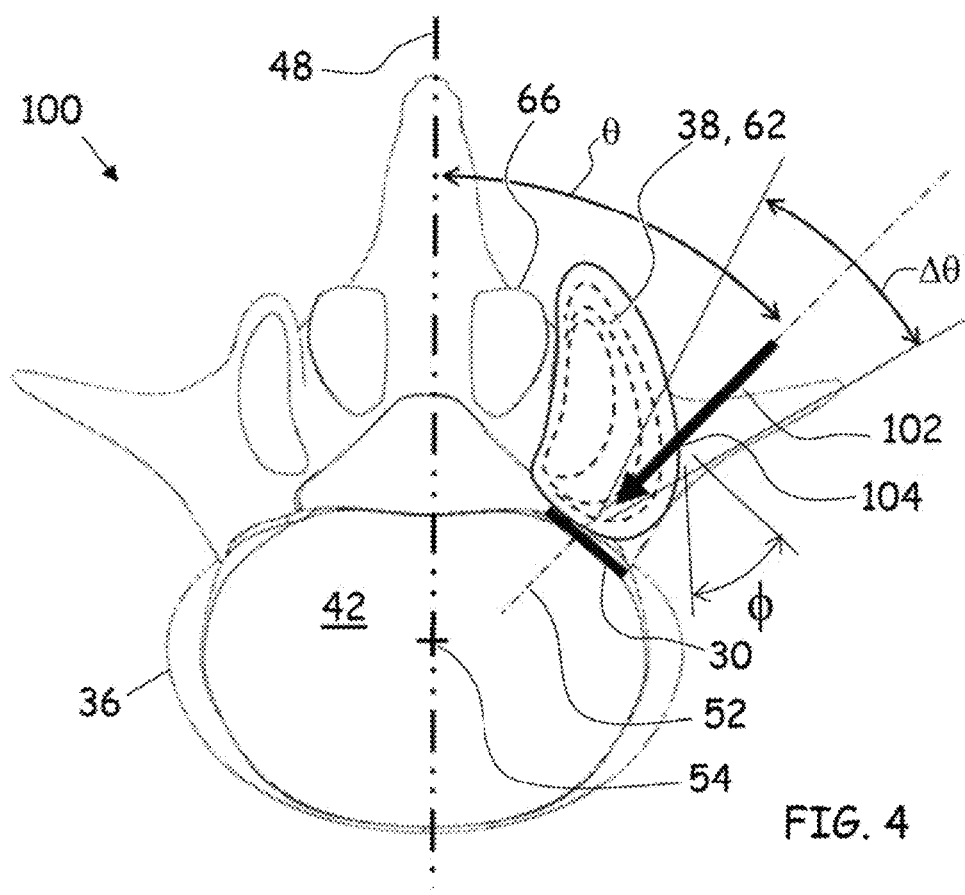
FIG. 4 is a sectional view at plane IV-IV of FIG. 3, depicting approaches for a trans-facet OLLIF procedure according to an embodiment of the disclosure.

Referring to FIG. 4, a trans-facet OLLIF layout 100 is depicted according to an embodiment of the disclosure. The trans-facet OLLIF layout 100 is characterized by many of the same aspects and attributes as the standard OLLIF layout (FIG. 2), some of which are indicated by same-labeled reference characters. The trans-facet OLLIF layout 100 includes a trans-facet approach 102 that passes through the bone 62 at a target site 104. For the layout 100, the bone or bone growth 62 is depicted as growth on the superior articular process 38. This aspect of the trans-facet layout 100 is for illustration and is non-limiting. That is, bone growth 62 may be present on other anatomical structures in the path of the trans-facet approach 102 to Kambin's triangle 30, including but not limited to the inferior articular process 66 of the superior vertebra 44 (FIG. 3).

While access for any approach angle θ may be forged using the trans-facet OLLIF technique, the approach variance Δθ is typically narrower than for standard OLLIF procedures, and is typically centered about the preferred approach angle θ of 45 degrees. In some situations, the obstruction of the bone 62 is such that the nominal approach angle θ of 45 degrees would cause grazing contact with the bone 62. In such situations, a surgeon implementing the trans-facet OLLIF technique may choose a smaller approach angle θ relative to the sagittal plane 48 for passing through the bone 62, thereby providing better registration of cutting tools on the bone 62 for a more predictable formation of the trans-facet approach 102.

Referring to FIGS. 5 and 6, instruments 120 for performing the trans-facet OLLIF procedure is depicted according to an embodiment of the disclosure. The instruments 120 include a sheathed electrophysiological (EP) probe assembly 122, a guide wire 124 (also referred to as a KIRSCHNER wire or k-wire), a tissue dilator 126, an access portal 128, a cannulated drill 132, an inner drill 134, and an electrical isolation barrier 136. For the depicted instruments 120, the electrical isolation barrier 136 is a dielectric sleeve 138. Some embodiments include an access portal handle 142 coupled to the access portal 128 and an auxiliary handle 144 for selective coupling to and manipulation of at least one of the tissue dilator 126, the cannulated drill 132, and the inner drill 134.

The sheathed EP probe assembly 122 includes an EP probe 152 removably disposed within a sheath 154, the EP probe 152 including an electrode 156 extendible through a distal end 158 of the sheath 154. The cannulated drill 132 defines a central passage 166 through which the inner drill 134 can be disposed. In some embodiments, the central passage 166 is configured for a close sliding fit with the inner drill 134. Herein, such "close sliding fit" is understood to be a fit that freely allows translation and rotation of the inner drill 134 within the central passage 166 without substantial play therebetween. In some embodiments, one or both of the cannulated drill 132 and the access portal 128 is a trephine.

A boring assembly 162 (FIG. 6) is configured with the access portal 128, the cannulated drill 132, the inner drill 134, and the electrical isolation barrier 136. The cannulated drill 132 is disposed in the access portal 128 and the inner drill 134 is disposed in the cannulated drill 132, with the cannulated drill 132 and inner drill 134 being extendable at a distal end 164 of the boring assembly 162. The electrical isolation barrier 136 may be arranged to electrically isolate at least the cannulated drill 132 from surrounding body tissue 168 along the approach 102 that radially surrounds the boring assembly 162 when inserted (FIGS. 15 through 23). For the depicted instruments 120, the electrical isolation barrier 136 is the dielectric sleeve 138 formed as a separate component and coupled to an exterior surface 172 of the access portal 128. Alternatively, the dielectric sleeve 138 may be configured for coupling to an interior surface 174 of the access portal or an exterior surface 176 of the cannulated drill 132. In some embodiments, the electrical isolation barrier 136 is a dielectric coating formed on one or more of the aforementioned surfaces 172, 174, 176. The dielectric sleeve 138 and/or dielectric coating may be a polymer. In some embodiments, the electrical isolation barrier 136 is formed by anodizing one or more of the surfaces 172, 174, 176.

Functionally, the EP probe 152 enables the surgeon to verify that the target site 104 is sufficiently electrophysiologically silent, for example, by measuring an ion current that is less than about 10 milliamp. The k-wire 124, in addition to guiding various tools to a target site 104, may define an impression 178 (FIG. 16) for seating and starting the inner drill 134 at the target site 104. The inner drill 134, in turn, can be bored into the target site 104 at the impression 178 and act as a pilot for the cannulated drill 132. The piloting aspect of the inner drill 134 prevents the cannulated drill 132 from slipping off the target site 104 when rotationally advanced, particularly when the target site 104 defines a steep incidence angle ϕ relative to the approach 102 (FIG. 4). The piloting arrangement of the inner drill 134 enables formation of a well-defined bore or channel 184 (FIG. 23) through the bone 62 that is concentric with the approach 102.

Figure 15:
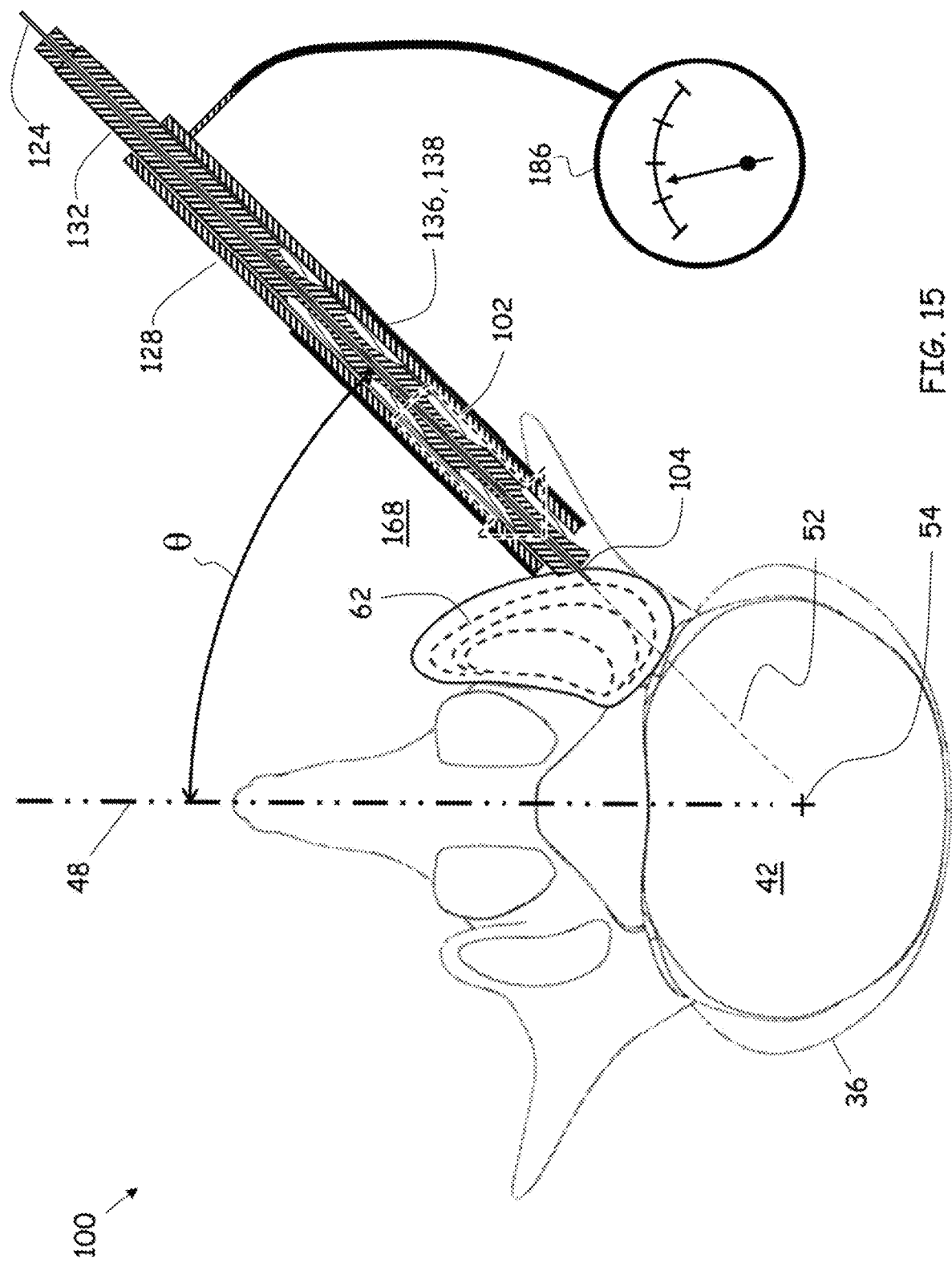

The electrical isolation barrier 136 acts to electrically isolate at least the cannulated drill 132 from the surrounding body tissue 168. Any component of the boring assembly 162 that is radially surrounded by the electrical isolation barrier 136 but electrically exposed at the contact of the target site 104 can serve as an electrode for detecting electrophysiological activity at the distal end 164 of the boring assembly, for example by connection to a neuromonitoring system 186 (FIG. 15). The electrophysiological monitoring enables the surgeon to verify electrophysiological silence as the bore or channel 184 is being formed.

In some embodiments, some or all of the instrumentation 120 is provided as a kit 190. The kit 190 may include instructions 192 for performing various steps of the trans-facet OLLIF procedure. The instructions 192 are provided on a tangible, non-transitory medium, and may be physically included with the kit 190 such as on a printed document (depicted), compact disc, or flash drive. Non-limiting examples of a tangible, non-transitory medium include a paper document and computer-readable media including compact disc and magnetic storage devices (e.g., hard disk, flash drive, cartridge, floppy drive). The computer-readable media may be local or accessible over the internet. The instructions 192 may be complete on a single medium, or divided among two or more media. For example, some of the instructions 192 may be written on a paper document that instruct the user to access one or more of the steps of the method over the internet, the internet-accessible steps being stored on a computer-readable medium or media. The instructions 192 may embody the techniques and methods depicted or described herein using text, photos, videos, or a combination thereof to instruct and guide the user. The instructions may be in the form of written words, figures, photos, video presentations, or a combination thereof to instruct and guide the user.

Figure 8:
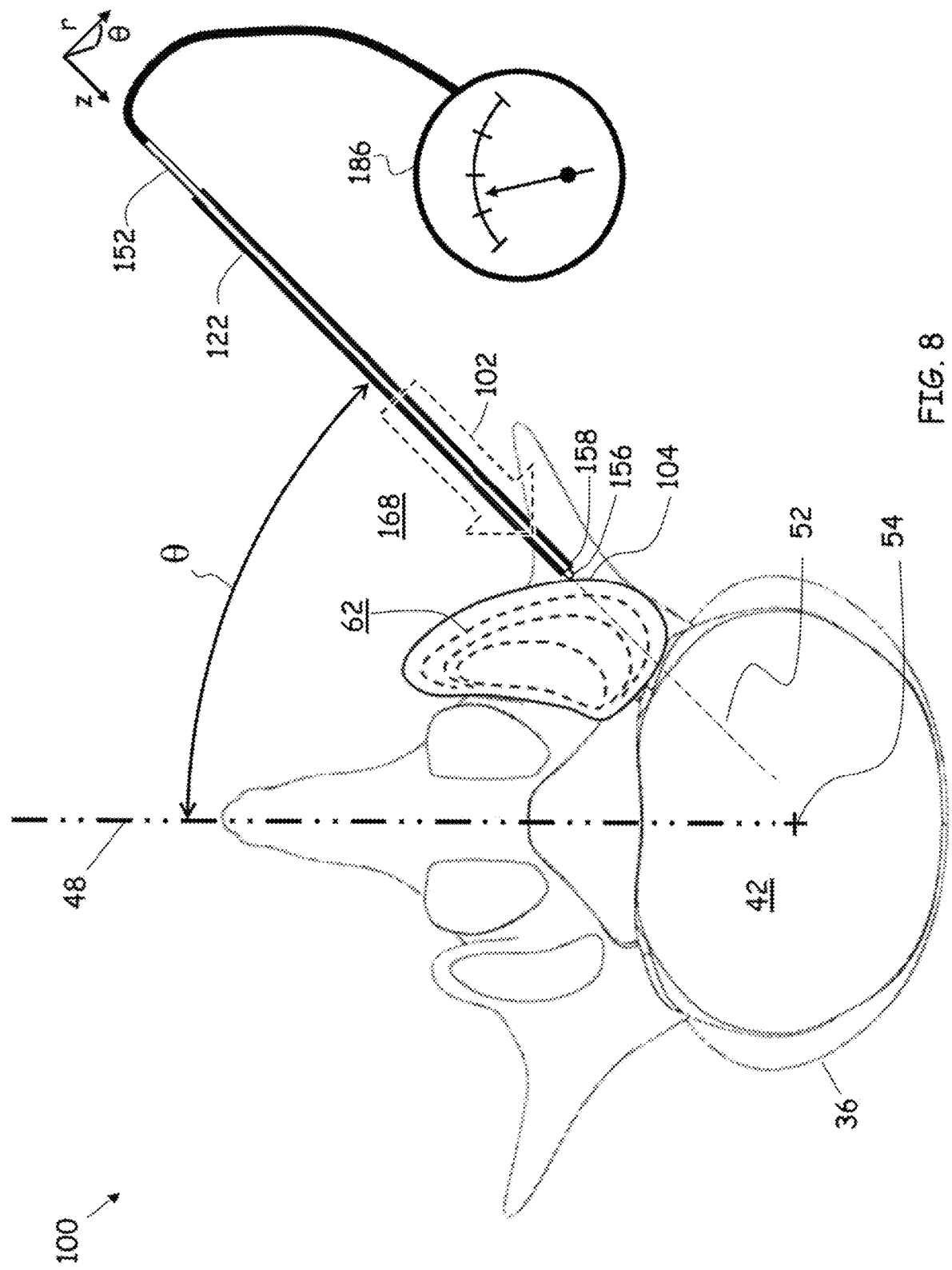

Referring to FIGS. 7 through 23, a preparation method 200 for preparing a patient for trans-facet OLLIF is depicted according to an embodiment of the disclosure. In some embodiments, the target site 104 is probed to verify the safety of the approach 102. The sheathed EP probe assembly 122 is inserted into the surgical incision (s202) and guided to the target site 104 at the desired trans-facet OLLIF approach 102 using standard operating procedures. The electrode 156 of the EP probe 152 is brought into contact with the target site 104 (s202) and the electrophysiological activity measured, for example with the neuromonitoring system 186 (s204; FIG. 8). If the ion current is at or below a predetermined threshold (e.g., 10 milliamps), the target site 104 is considered safe for proceeding.

Figure 9:
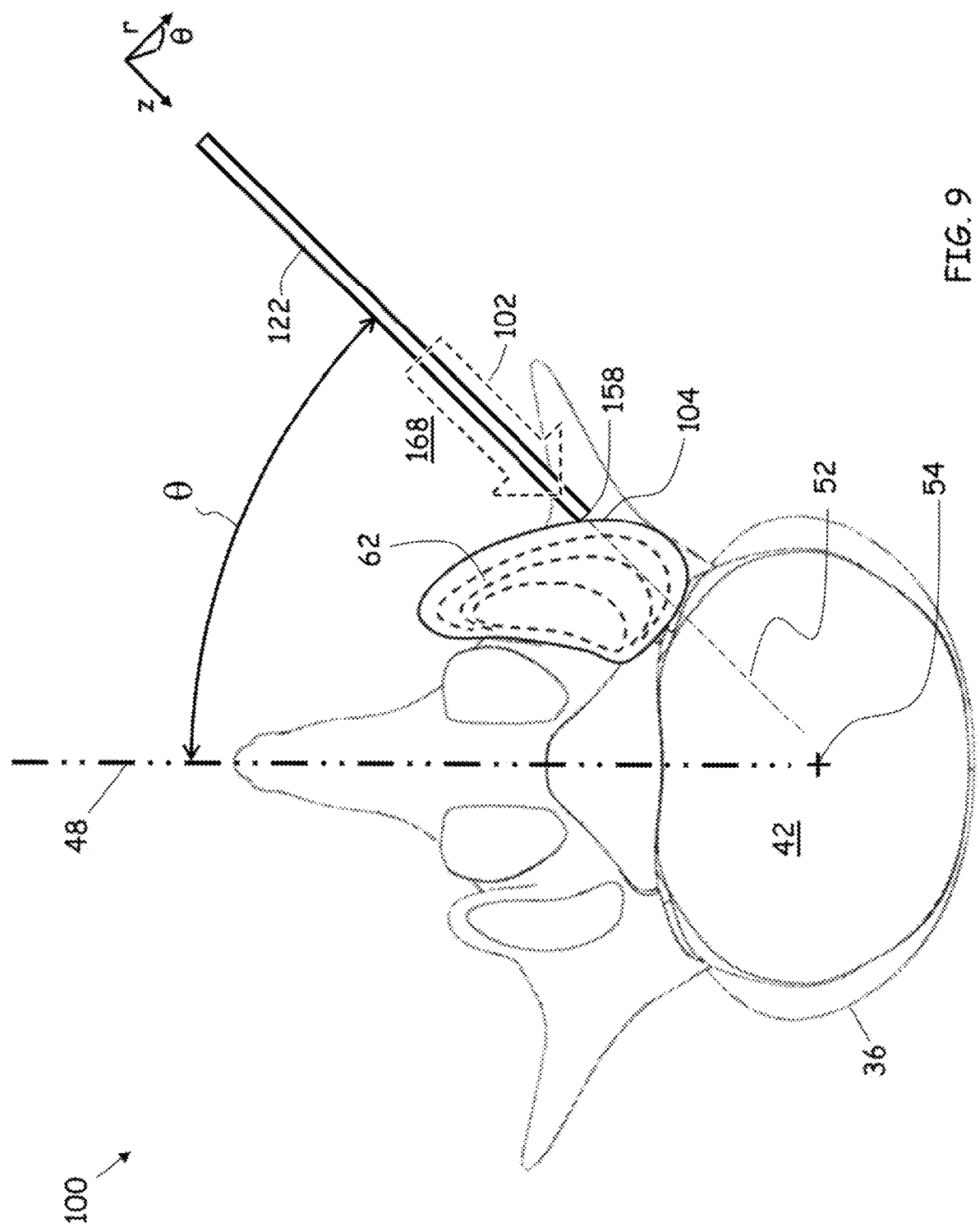
Figure 10:
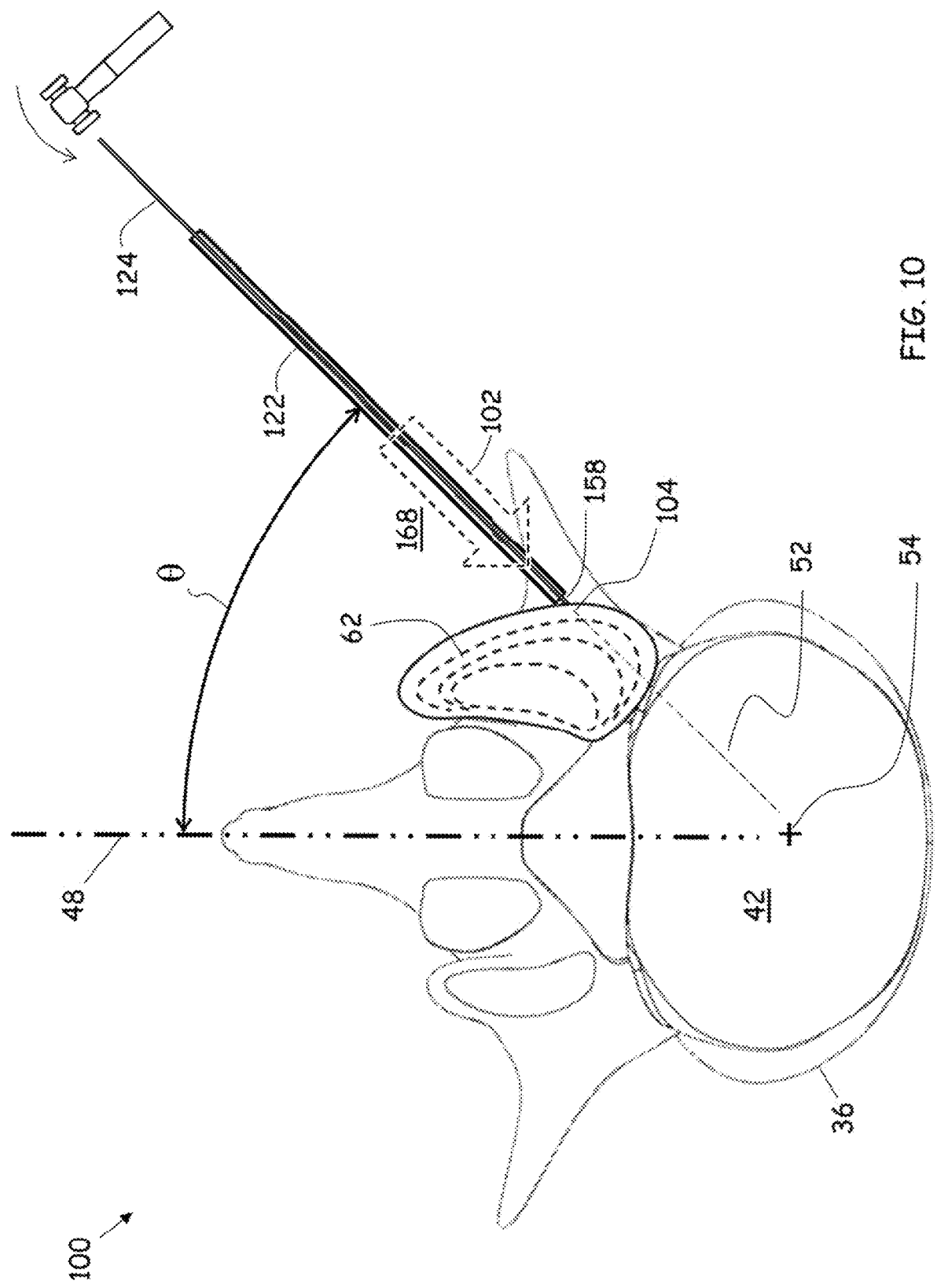
Figure 11:
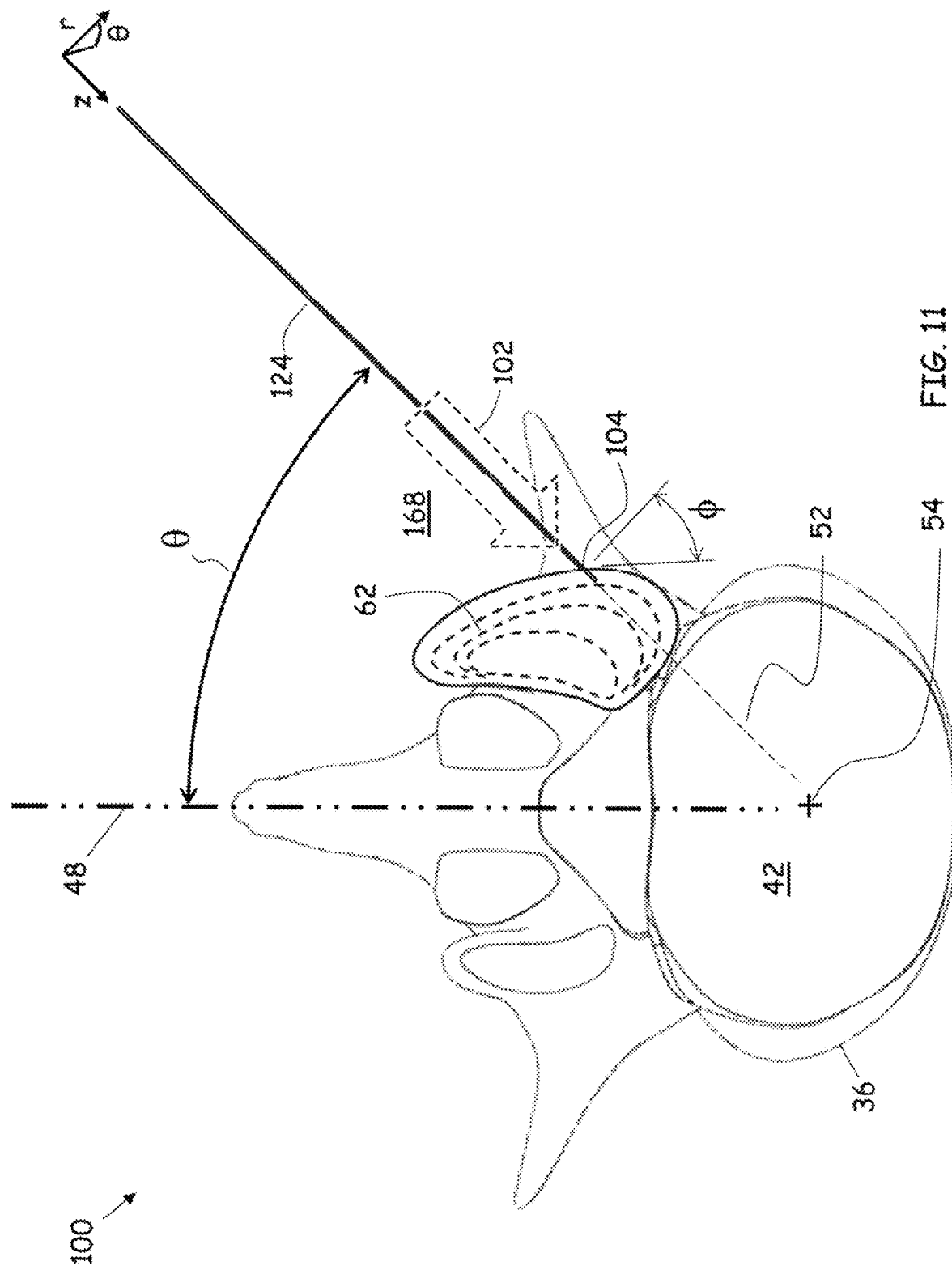

The EP probe 152 may be removed from the sheath 154, leaving the distal end 158 of the sheath 154 at the target site 104 (s206; FIG. 9). In some embodiments, the sheath 154 is registered against the bone 62 to maintain at least approximate alignment of the sheath 154 along the approach 102. The k-wire 124 is inserted through the sheath 154 and brought into contact with the target site 104 (s208). In some embodiments, the k-wire 124 is set into the target site 104 (s210), for example by a light tapping engagement with the k-wire 124 (FIG. 10). The sheath 154 is removed (s212), leaving only the k-wire 124 (FIG. 11). If the k-wire 124 is sufficiently set in the target site 104 (e.g., at a depth of one to three millimeters), the k-wire can maintain the approach 102 to the target site 104.

Figure 12:
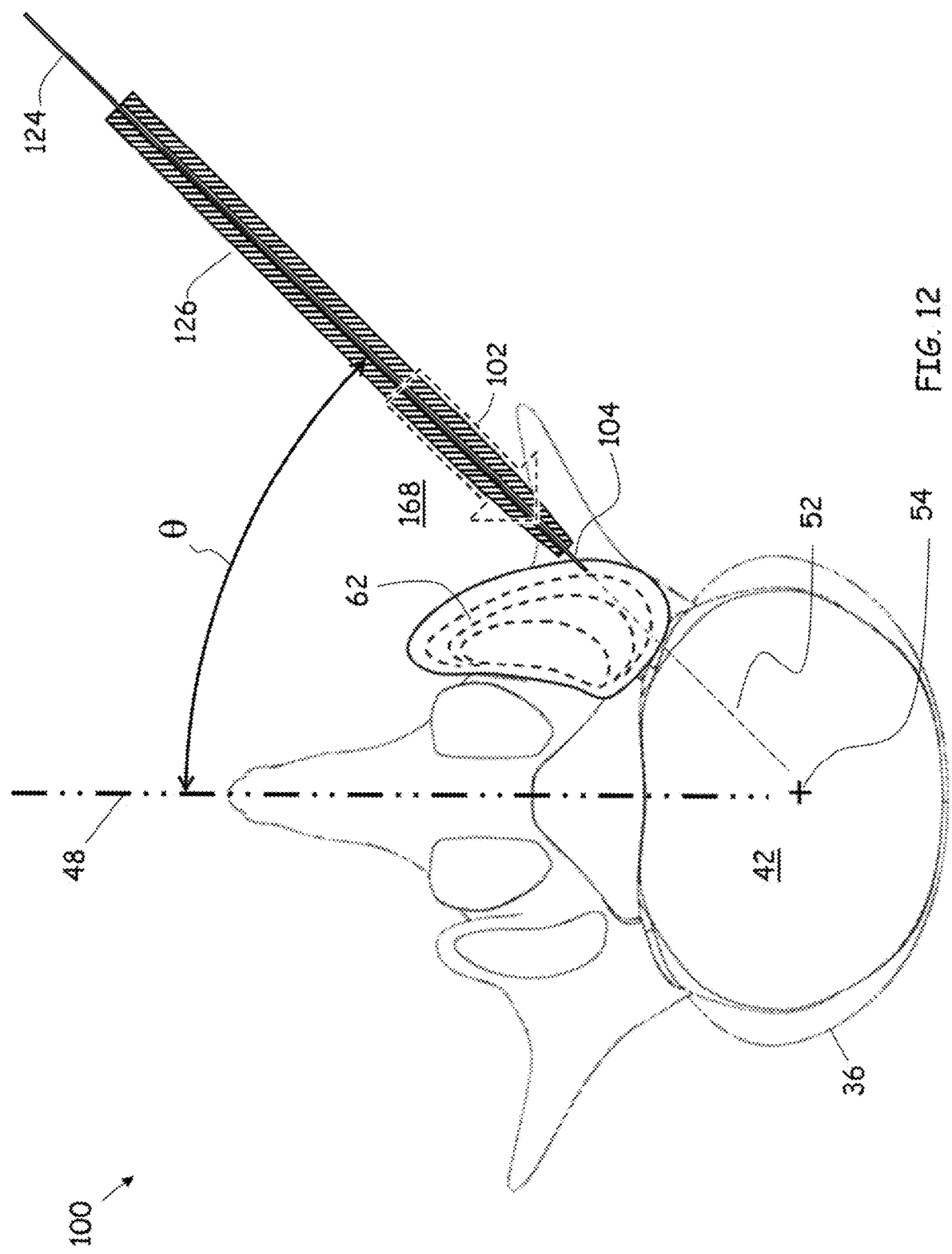
Figure 13:
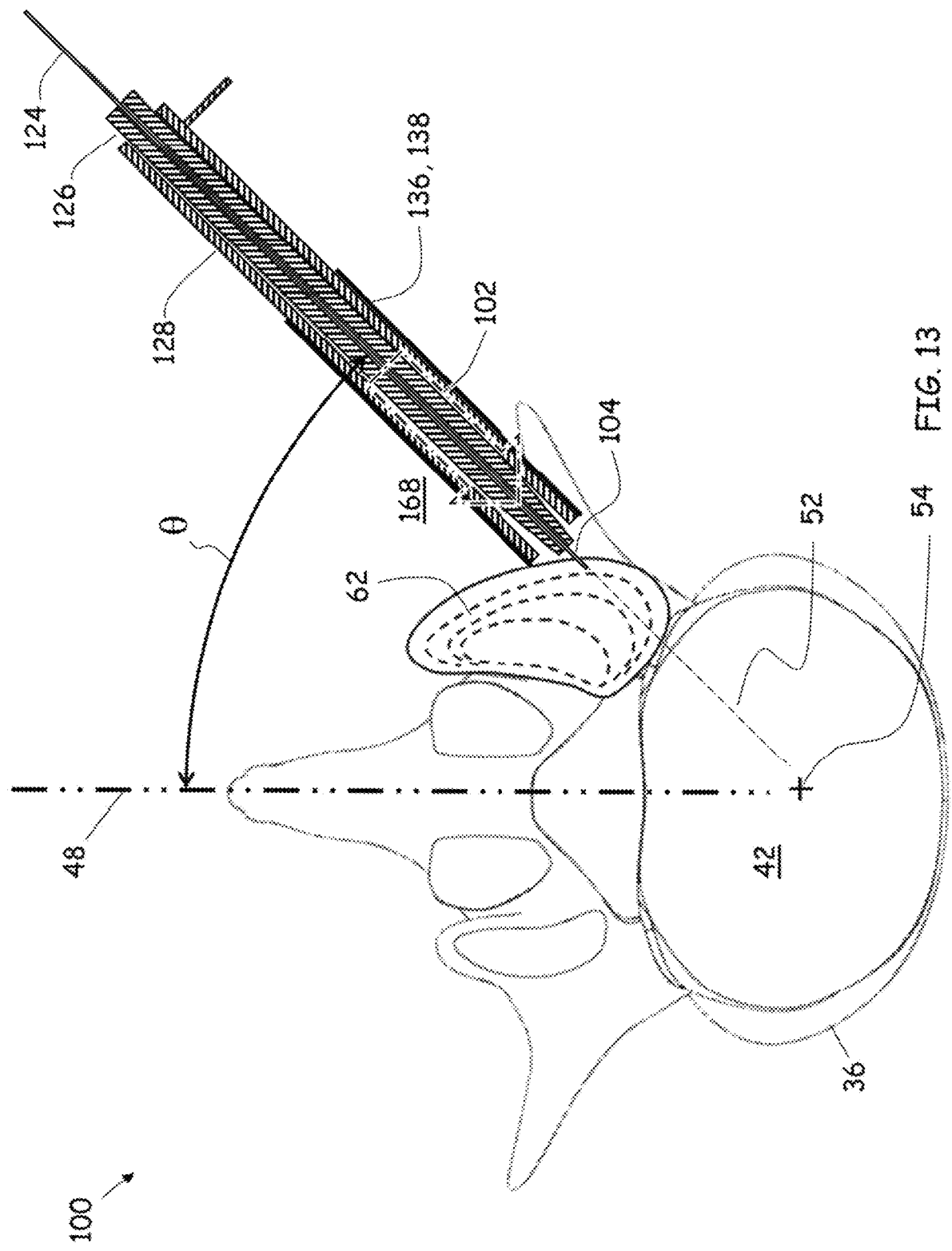
Figure 14:
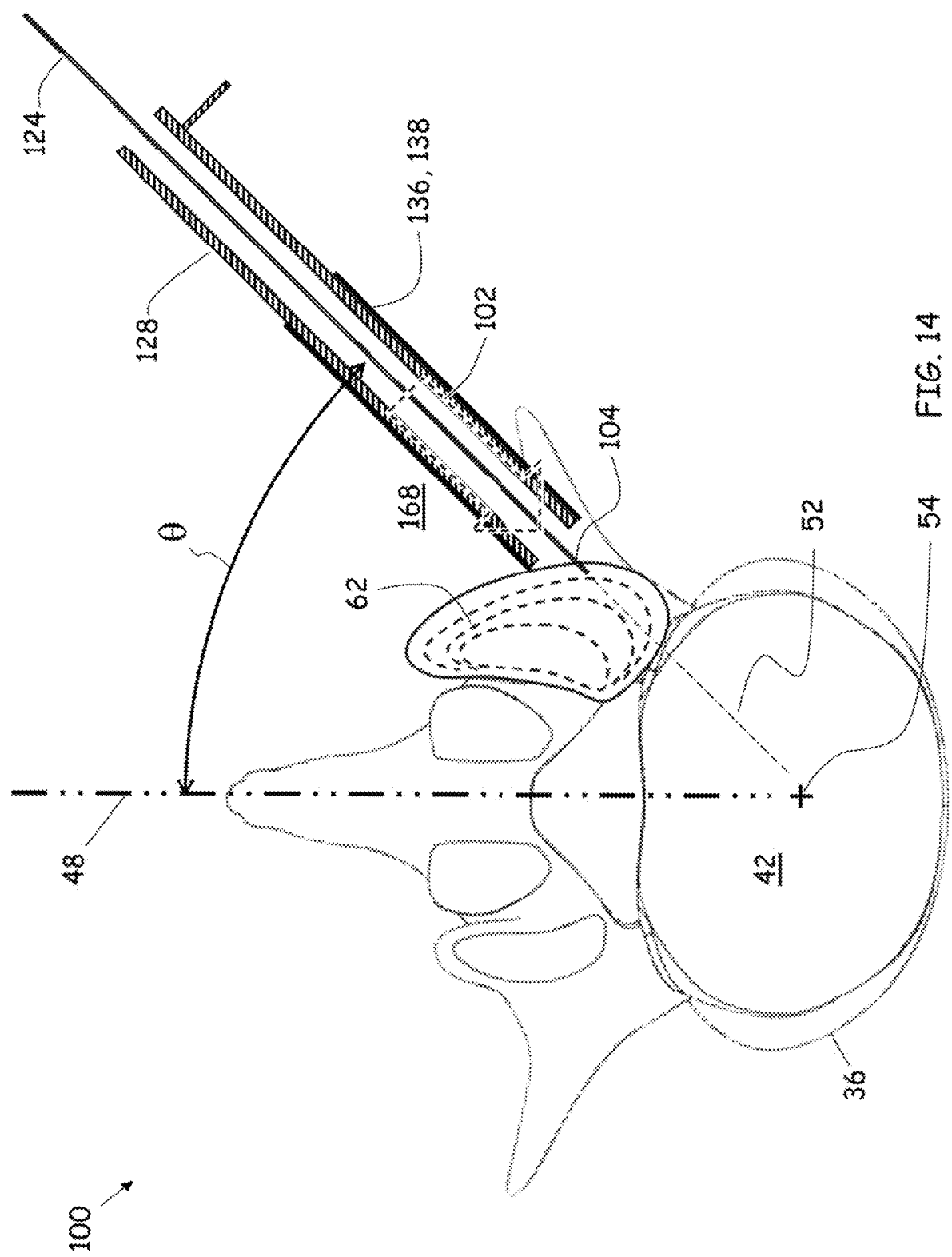

In some embodiments, the tissue dilator 126 is inserted over the k-wire 124 (s214) and may be brought into contact or near contact with the target site 104 (FIG. 12). The tissue dilator acts to dilate the surrounding body tissue 168 along the approach 102. With the tissue dilator 126 in place along the approach 102, the access portal 128 is slid over the tissue dilator 126 (s216) and may be brought into contact with the bone 62 (FIG. 13). The tissue dilator 126 is removed (s218; FIG. 14), and the cannulated drill 132 is slid over the k-wire 124 into the access portal 128 (s220) and brought into contact with the target site 104 (FIG. 15).

The cannulated drill 132 is electrically isolated from the surrounding body tissue 168 (s222), which may be accomplished in several ways. In the depicted embodiment, the electrical isolation barrier 136 is the dielectric sleeve 138 coupled to the exterior surface 172 of the access portal 128. As discussed above, the electrical isolation barrier 136 may be provided by one of several components, such as the dielectric sleeve 138, or by coating or anodizing one or both of the interior or exterior surfaces 174, 172 of the access portal and/or the exterior surface 176 of the cannulated drill 132. Whichever of the dielectric sleeve 138 or surfaces 172, 174,176 bearing the electrical isolation barrier 136, the electrical isolation step s222 is accomplished by assembly of the associated component into the boring assembly 162. In FIGS. 15 through 22, the neuromonitoring system 186 is depicted as being electrically coupled with the access portal 128. However, the neuromonitoring system 186 may be electrically coupled with any component that is electrically isolated from the surrounding body tissue 168 by the electrical isolation barrier 136 to the same effect.

The electrophysiological activity of the target site 104 may be measured using the partially assembled boring assembly 162 (FIG. 15). The components of the boring assembly 162 that are electrically isolated from the surrounding body tissue 168 and in contact with the target site 104 act as an electrode for measurement with, for example, the neuromonitoring system 186. For the FIG. 15 configuration, because the electrical isolation barrier 136 surrounds the exterior surface 172 of the access portal 128, the components that can sense electrophysiological activity include the access portal 128, the cannulated drill 132, and the k-wire 124. For embodiments where electrical isolation barrier 136 is disposed on the interior surface 174 of the access portal 128 or on the exterior surface 176 of the cannulated drill 132, the components sensitive to electrophysiological activity are limited to the cannulated drill 132 and the k-wire 124. By measuring the ion current at the target site 104 with the partially assembled boring assembly 162, the surgeon can verify the electrophysiological silence of the target site 104 (s224).

Figure 16:
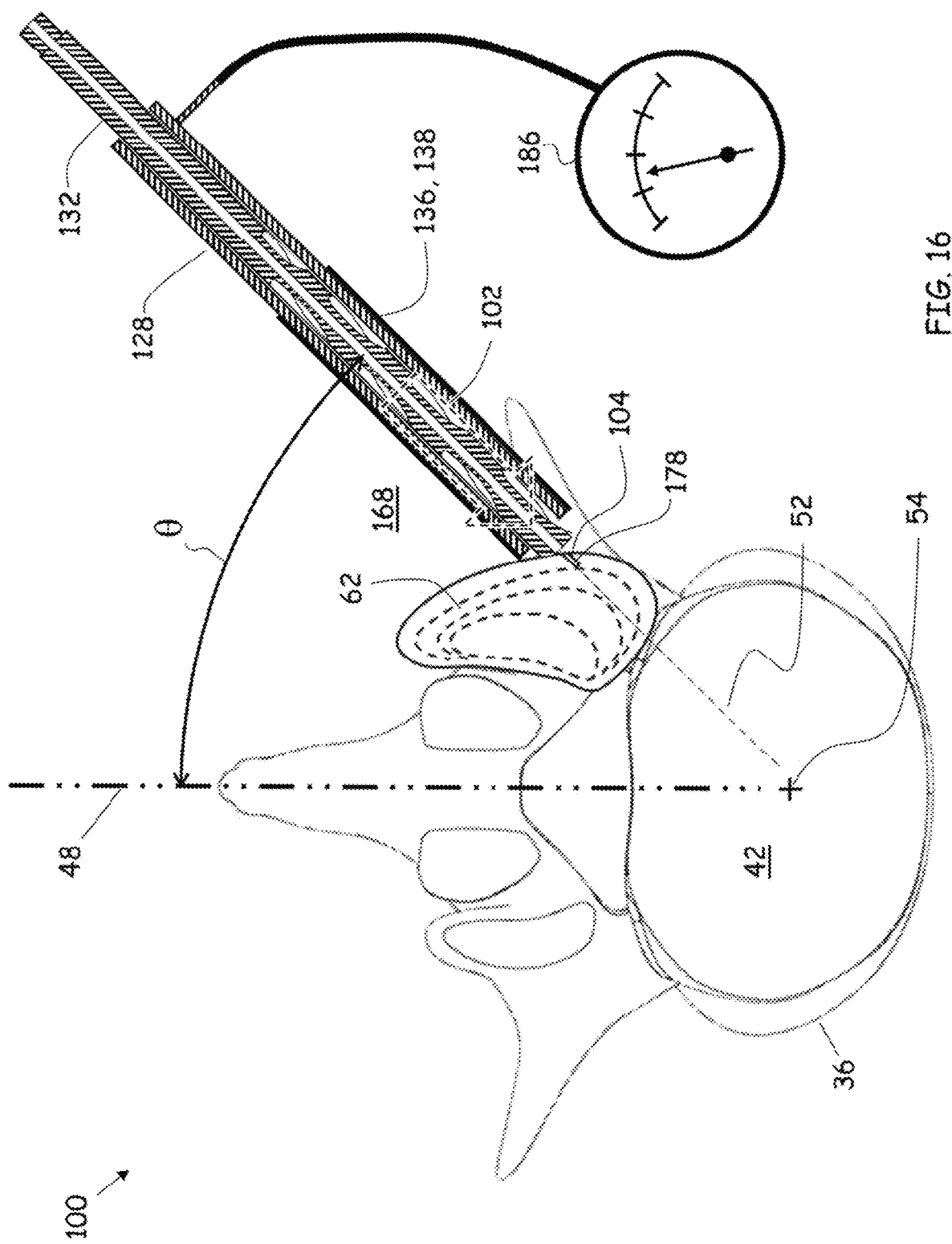
Figure 17:
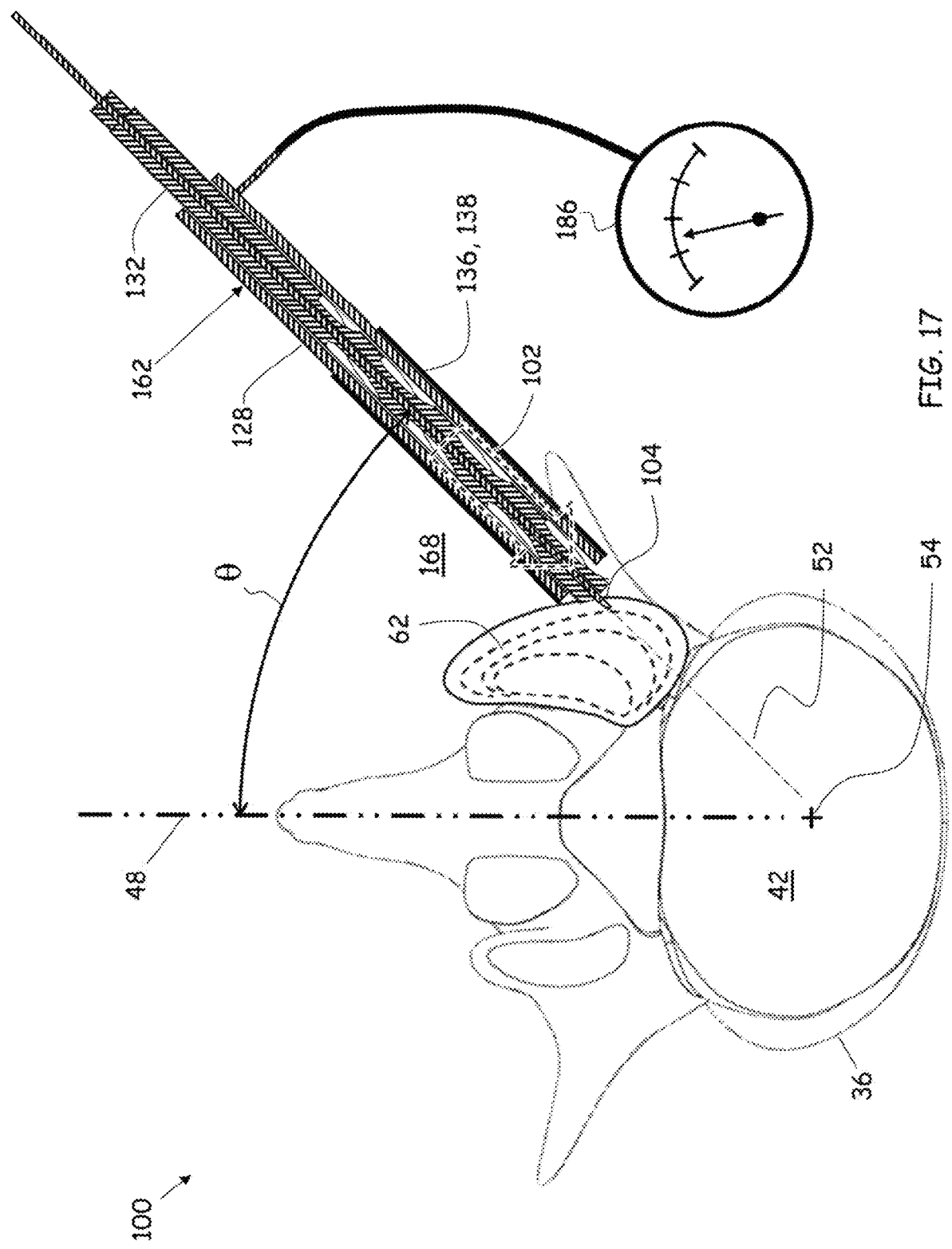

The k-wire 124 is removed from the cannulated drill 132, leaving the impression 178 at the target site 104 (s226; FIG. 16). The cannulated drill 132 and/or sheath 154 may be registered against the bone 62 prior to removal of the k-wire 124 to maintain at least approximate alignment of the partially assembled boring assembly 162 along the approach 102. The inner drill 134 is inserted through the central passage 166 of the cannulated drill 132 (s228) and set into the target site 104 (s230), for example by being driven into the impression 178 made by the k-wire 124 (FIG. 17). The inner drill 134, being isolated from the surrounding body tissue 168 by the electrical isolation barrier 136, is part of the boring assembly 162 that is sensitive to electrophysiological activity of the target site 104. The ion current at the contact of the target site 104 may be measured, for example, using the neuromonitoring system 186, to verify the electrophysiological silence of the target site 104 (s232).

Figure 18:
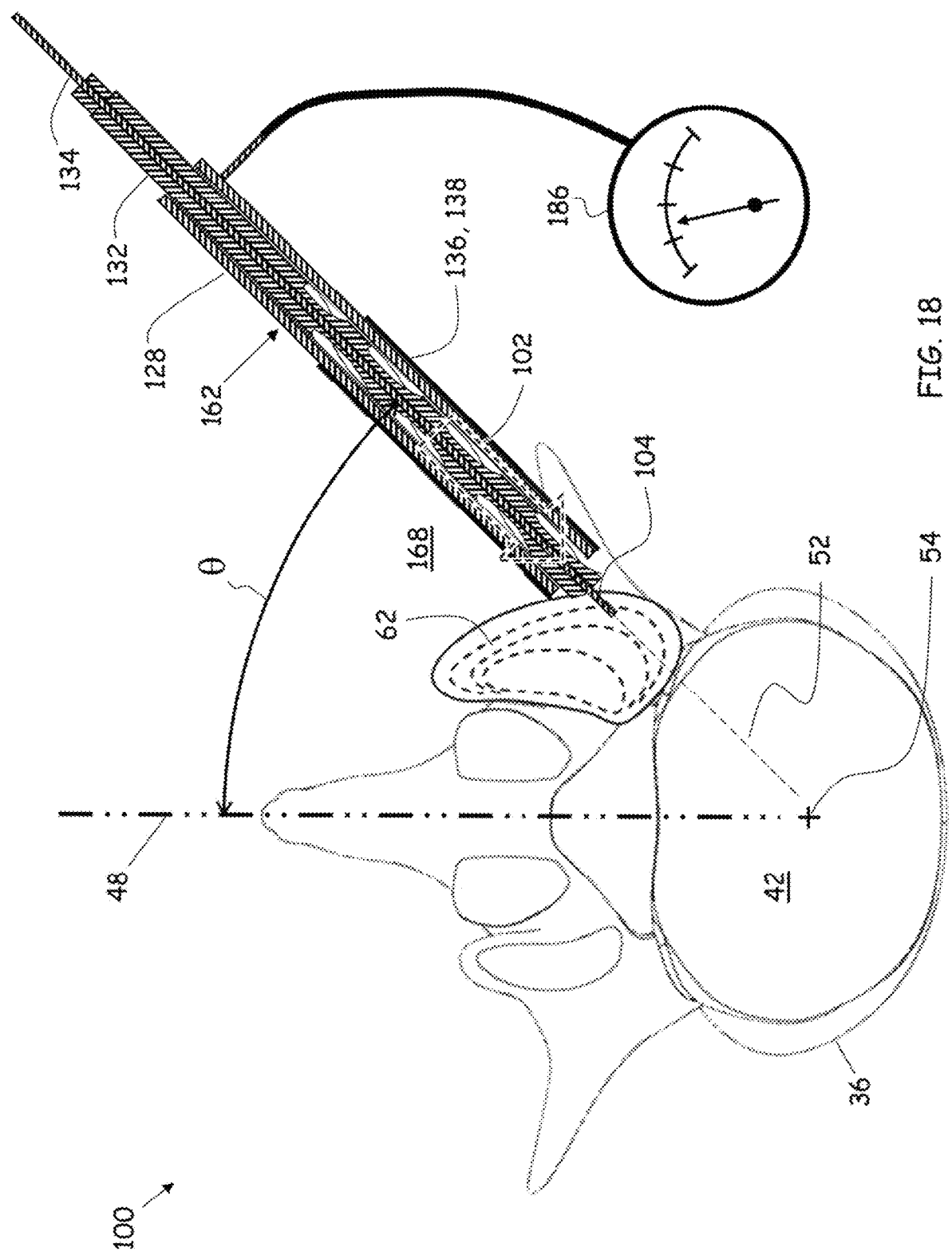
Figure 19:
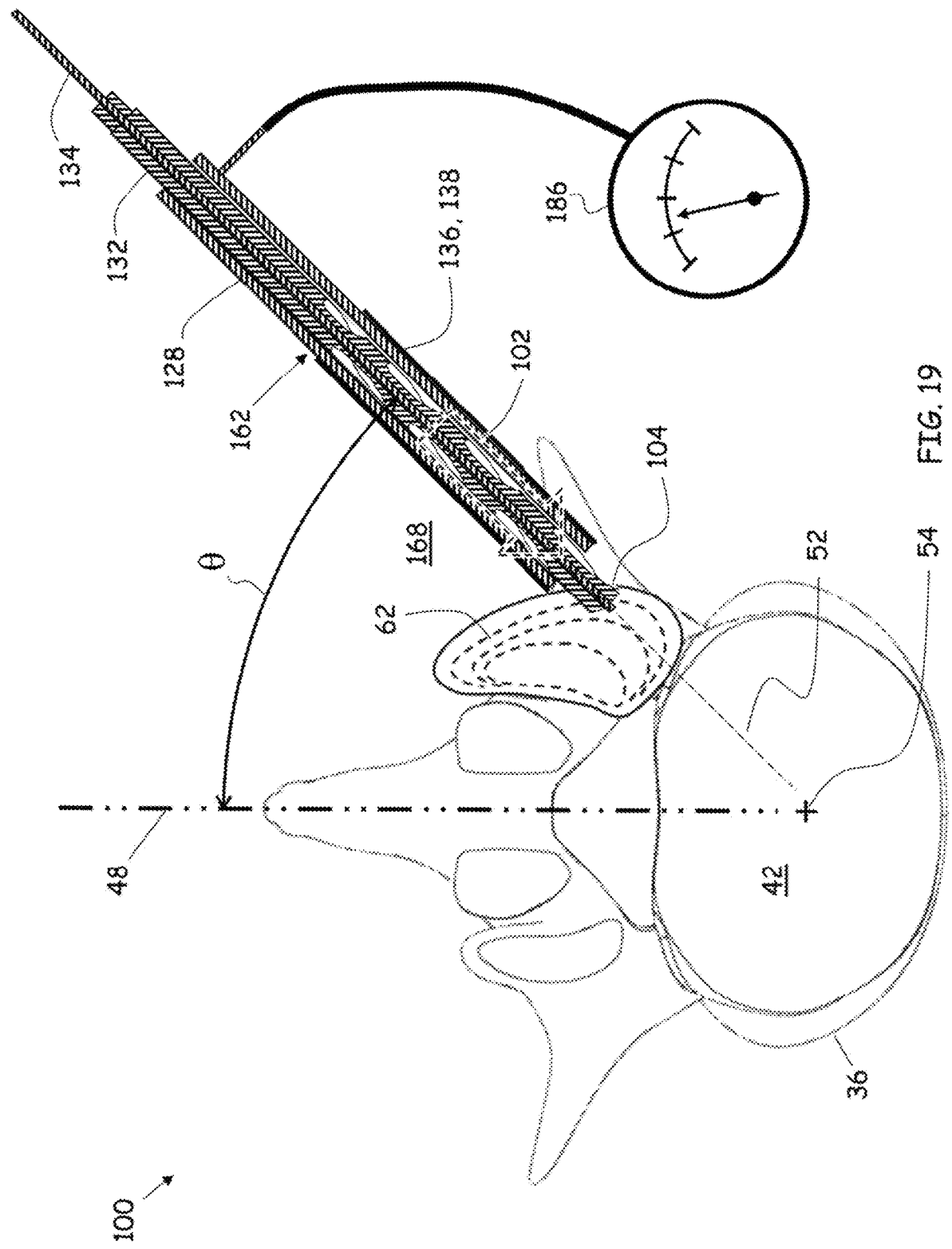

With the boring assembly 162 being completed in-situ (FIG. 17), formation of the bore or channel 184 may commence. The formation of the bore or channel 184 may include iteratively advancing the inner drill 134 (s234; FIG. 18), the cannulated drill 132 (s238; FIG. 19), and the access portal 128 (s242; FIG. 20) into the bone 62, while intermittently checking and verifying the electrophysiological silence of the contact of the boring assembly 162 with the target site 104 (s232, s236, and s240). Any given advance of the inner drill 134, cannulated drill 132, and access portal 128 may be incremental, herein defined as being within a range 0.5 to 3 millimeters inclusive along the approach 102. Herein, a range that is said to be "inclusive" includes the endpoints of the stated range.

As the boring assembly 162 is advanced, so is the attendant electrical isolation barrier 136. Steps s232 through s242 are repeated in an iterative loop (L244) until the bore or channel 184 traverses through the bone 62, providing access to Kambin's triangle 30 (FIG. 21). During execution of the iterative loop L244, the inner and cannulated drills 134, 132 are advanced by rotation to execute the drilling action. In some embodiments, the access portal 128 is advanced by rotation, particularly where the access portal 128 is a trephine. The access portal 128 may also be advanced by tapping on the proximal end in the direction of the approach 102.

Upon completion of the bore or channel 184, the inner drill 134 is removed from the boring assembly 162 and replaced with the k-wire 124 (s246; FIG. 22). The cannulated drill 132 is removed over the k-wire 124 (s248), so that only the k-wire 124 and the access portal 128 remain in the bore or channel 184 (FIG. 23). The k-wire 124 and access portal 128 may then be utilized to proceed with aspects of the standard OLLIF procedure (s250), such as dilation to expand Kambin's triangle 30, inserting the access portal 128 into the disc space, performing a discectomy, preparation of the vertebral endplates, and insertion of spinal implants.

Each of the additional figures and methods disclosed herein can be used separately, or in conjunction with other features and methods, to provide improved devices and methods for making and using the same. Therefore, combinations of features and methods disclosed herein may not be necessary to practice the disclosure in its broadest sense and are instead disclosed merely to particularly describe representative and preferred embodiments.

Various modifications to the embodiments may be apparent to one of skill in the art upon reading this disclosure. For example, persons of ordinary skill in the relevant arts will recognize that the various features described for the different embodiments can be suitably combined, un-combined, and re-combined with other features, alone, or in different combinations. Likewise, the various features described above should all be regarded as example embodiments, rather than limitations to the scope or spirit of the disclosure.

Persons of ordinary skill in the relevant arts will recognize that various embodiments can comprise fewer features than illustrated in any individual embodiment described above. The embodiments described herein are not meant to be an exhaustive presentation of the ways in which the various features may be combined. Accordingly, the embodiments are not mutually exclusive combinations of features; rather, the claims can comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

Unless indicated otherwise, references to "embodiment(s)", "disclosure", "present disclosure", "embodiment(s) of the disclosure", "disclosed embodiment(s)", and the like contained herein refer to the specification (text, including the claims, and figures) of this patent application that are not admitted prior art.

For purposes of interpreting the claims, it is expressly intended that the provisions of 35 U.S.C. 112(f) are not to be invoked unless the specific terms "means for" or "step for" are recited in the respective claim.

What is claimed is:

1. A method of preparing a patient for spinal fusion using a trans-facet approach, comprising:
   providing a kit that includes a boring assembly, said boring assembly including
      an inner drill,
      a cannulated drill defining a central axis and a central through-passage concentric about said central axis, said central through-passage being configured to receive said inner drill, and
      an electrical isolation barrier radially surrounding said cannulated drill;
   providing a set of instructions on a tangible, non-transitory medium, said instructions comprising:
      advancing said inner drill into a bone at an approach angle that defines a trajectory that passes through Kambin's triangle;
      advancing said cannulated drill into said bone over said inner drill;
      advancing an access portal into said bone over said cannulated drill;
      intermittently measuring electrophysiological activity at a distal end of said boring assembly during the steps of advancing; and
      repeating the steps of advancing and intermittently measuring to form a bore or channel through said bone for access to Kambin's triangle.

2. The method of claim 1, wherein the instructions provided in the step of providing said set of instructions includes:
   comparing a measured value of said electrophysiological activity to a predetermined value; and
   proceeding with the step of repeating if said measured value is less than said predetermined value.

3. The method of claim 2, wherein the instructions provided in the step of providing said set of instructions establishes said predetermined value at 10 milliamp of ion current.

4. The method of claim 1, wherein the instructions provided in the step of providing said set of instructions includes incremental advancement of said inner drill, said cannulated drill, and said access portal.

5. The method of claim 4, wherein the instructions provided in the step of providing said set of instructions establishes said incremental advancement to be within a range of 0.5 to 3 millimeters inclusive.

6. The method of claim 1, wherein said kit provided in the step of providing said kit includes said access portal configured to receive said cannulated drill.

7. The method of claim 1, wherein the instructions provided in the step of providing said set of instructions includes:
   measuring electrophysiological activity at a target of said bone with an electrophysiological probe;
   removing said electrophysiological probe from a sheath to leave said sheath aligned with said target;
   inserting a guide wire into said sheath;
   setting said guide wire into said target; and
   removing said sheath over said guide wire.

8. The method of claim 7, wherein said kit provided in the step of providing said kit includes said electrophysiological probe.

9. The method of claim 7, wherein said kit provided in the step of providing said kit includes said sheath.

10. The method of claim 7, wherein said kit provided in the step of providing said kit includes an electrophysiological probe assembly that includes said electrophysiological probe and said sheath.

11. The method of claim 7, wherein said kit provided in the step of providing said kit includes said guide wire.

12. The method of claim 1, wherein the instructions provided in the step of providing said set of instructions includes:
   inserting said cannulated drill over said guide wire;
   electrically isolating said cannulated drill from surrounding tissue; and
   removing said guide wire from said cannulated drill, leaving said cannulated drill aligned with said target.

13. The method of claim 1, wherein the instructions provided in the step of providing said set of instructions includes:
   removing said inner drill from said cannulated drill;
   inserting a guide wire into said cannulated drill; and
   removing said cannulated drill over said guide wire.

14. The method of claim 1, wherein the instructions provided in the step of providing said set of instructions includes proceeding with a spinal fusion process via said access to Kambin's triangle.

15. The method of claim 1, wherein the instructions provided in the step of providing said set of instructions includes proceeding with an OLLIF procedure via said access to Kambin's triangle.

16. The method of claim 1, wherein said cannulated drill provided in the step of providing said kit is a trephine.

17. The method of claim 1, wherein said access portal is provided in said kit and wherein said electrical isolation barrier provided in the step of providing said kit is integral with an outer surface of said access portal.

18. The method of claim 1, wherein said access portal is provided in said kit and wherein said electrical isolation barrier provided in the step of providing said kit is integral with an inner surface of said access portal.

19. The method of claim 1, wherein said electrical isolation barrier provided in the step of providing said kit is integral with an exterior surface of said cannulated drill.

20. The method of claim 1, wherein:
   said kit provided in the step of providing said kit includes an electrophysiological probe assembly; and
   the instructions provided in the step of providing said set of instructions includes performing the step of intermittently measuring electrophysiological activity with said electrophysiological probe assembly.

21. The method of claim 20, wherein the step of intermittently measuring electrophysiological activity provided in the step of providing said set of instructions is performed with said electrophysiological probe assembly.

22. The method of claim 1, wherein the instructions provided in the step of providing said set of instructions includes:
   inserting a dilator over said guide wire;
   inserting said access portal over said guide wire; and
   removing said dilator from said access portal, leaving said access portal aligned with said target.

23. The method of claim 22, wherein said kit provided in the step of providing said kit includes said dilator.

24. The method of claim 1, further comprising executing all of the instructions in said set of instructions.

* * * * *